United States Patent
Zou et al.

(10) Patent No.: US 10,806,759 B2
(45) Date of Patent: Oct. 20, 2020

(54) CHRISTENSENELLA INTESTINIHOMINIS AND APPLICATION THEREOF

(71) Applicant: BGI SHENZHEN, Shenzhen (CN)

(72) Inventors: Yuanqiang Zou, Shenzhen (CN); Wenbin Xue, Shenzhen (CN); Mei Lv, Shenzhen (CN); Liang Xiao, Shenzhen (CN); Xiaoping Li, Shenzhen (CN); Jinghong Yu, Shenzhen (CN); Chuan Liu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 0 days.

(21) Appl. No.: 16/082,873

(22) PCT Filed: Sep. 6, 2016

(86) PCT No.: PCT/CN2016/098247
§ 371 (c)(1),
(2) Date: Apr. 23, 2019

(87) PCT Pub. No.: WO2018/045493
PCT Pub. Date: Mar. 15, 2018

(65) Prior Publication Data
US 2019/0282633 A1  Sep. 19, 2019

(51) Int. Cl.
| | | |
|---|---|---|
| *A61K 35/74* | (2015.01) | |
| *A23L 33/135* | (2016.01) | |
| *A61K 35/741* | (2015.01) | |
| *A61P 3/04* | (2006.01) | |
| *C12N 1/20* | (2006.01) | |
| *A23C 9/12* | (2006.01) | |
| *A61K 35/00* | (2006.01) | |

(52) U.S. Cl.
CPC .......... *A61K 35/741* (2013.01); *A23L 33/135* (2016.08); *A61K 35/74* (2013.01); *A61P 3/04* (2018.01); *C12N 1/20* (2013.01); *A23C 9/1203* (2013.01); *A23V 2002/00* (2013.01); *A61K 2035/115* (2013.01)

(58) Field of Classification Search
CPC .................. A61K 35/741; A61K 35/74; A61K 2035/115; C12N 1/20; A61P 3/04; A23L 33/135; A23V 2002/00; A23C 9/1203; C12R 1/01
USPC ...................................... 424/93.4
See application file for complete search history.

(56) References Cited

FOREIGN PATENT DOCUMENTS

| | | |
|---|---|---|
| JP | 2014505467 A | 3/2014 |
| WO | 2015/164555 A1 | 10/2015 |

OTHER PUBLICATIONS

Watawana, M.I. et al. 2015. Health, Wellness, and Safety Aspects of the Consumption of Kombucha. Journal of Chemistry. Article ID: 591869. 11 pages. (Year: 2015).*
Harvard Health Publishing: Harvard Medical School. Publish 2009, updated 2019. Why People Become Overweight. https://www.health.harvard.edu/staying-healthy/why-people-become-overweight (Year: 2009).*
Mayo Clinic Staff. Strategies to Prevent Heart Disease. Mayo Clinic. Retrieved from: https://www.mayoclinic.org/diseases-conditions/heart-disease/in-depth/heart-disease-prevention/art-20046502 (Year: 2020).*
Dowshen, S. 2018. Can Diabetes Be Prevented?. Retrieved from: https://kidshealth.org/en/parents/prevention.html (Year: 2018).*
Morotomi et al., "Description of *Christensenella minuta* gen. nov., sp. nov., isolated from human faeces, which forms a distinct branch in the order *Clostridiales*, and proposal of Christensenellaceae fam. nov.," *International Journal of Systematic and Evolutionary Microbiology* 62:144-149 (2012).
Office Action issued for JP application 2018-546803, dated Nov. 12, 2019.
Zou, Y. et al, Database GenBank [online], Accession No. KX078376, Jul. 31, 2016 uploaded, [retrieved on Oct. 29, 2019], <https://www.ncbi.nlm.nih.gov/nuccore/KX078376.1?report=gbwithparts&log$=seqview>, Definition: *Christensenella* sp.AF73-05CM02 16S ribosomal RNA gene, partial sequence.

* cited by examiner

*Primary Examiner* — Michelle F. Paguio Frising
*Assistant Examiner* — Kasandra S Hunter
(74) *Attorney, Agent, or Firm* — Westman, Champlin & Koehler, P.A.; Z. Peter Sawicki; Amanda M. Prose (57) ABSTRACT

Provided are *Christensenella intestinihominis* and an application thereof, specifically, use of *Christensenella intestinihominis* in treating and preventing obesity and related diseases thereof. Also provided are a composition for treating and preventing obesity and related diseases thereof, comprising compositions of drugs, drinks, food, or animal feed, and a method for reducing weight and/or blood lipid.

19 Claims, 2 Drawing Sheets

Specification includes a Sequence Listing.

CHRISTENSENELLA INTESTINIHOMINIS AND APPLICATION THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 140214_403USPC_SEQUENCE_LISTING.txt. The text file is 2.5 KB, was created on Sep. 6, 2018, and is being submitted electronically via EFS-Web.

TECHNICAL FIELD

The present invention relates to the field of microbiology, and in particular to the use of *Christensenella intestinihominis* for the treatment and prevention of obesity and related diseases, and to a composition comprising *Christensenella intestinihominis* and the use thereof.

BACKGROUND

A large number of symbiotic microorganisms are inhabited in the human intestinal tract, most of which are beneficial to the human body. These microorganisms not only cooperate with the host for the metabolism of matter and energy, but also play an important role in maintaining the health of the host. At present, many studies at home and abroad have revealed that intestinal microorganisms are closely related to inflammatory and metabolic diseases such as irritable bowel syndrome (IBS), ulcerative enteritis (UC), obesity, and type 2 diabetes. By the research and development of intestinal probiotics, it is possible to effectively treat and prevent diseases caused by intestinal microbial imbalance, especially intestinal inflammatory and metabolic diseases caused by flora disorder.

Short-chain fatty acids, including acetic acid, propionic acid, butyric acid, pentanoic acid, etc., are metabolites produced by certain types of bacteria in the intestine. The production of short-chain fatty acids plays an important role in the maintenance of intestinal health. Studies have shown that there is a significant difference in the content of short-chain fatty acid-producing bacteria, such as *Roseburia, Faecalibacterium, Eubacterium* rectale, etc., between the intestine of healthy people and the intestine of patients with type 2 diabetes.

Cholesterol is of great significance to the human body as a precursor of vitamin D synthesis. But because of the unreasonable diets for most people, it is easy to cause excessive cholesterol in the body, especially in the blood, thereby causing obesity, diabetes and a series of cardiovascular and cerebrovascular diseases, such as coronary heart disease, atherosclerosis, etc. Therefore, the reduction of cholesterol in the body is an effective way to prevent cardiovascular and cerebrovascular diseases.

The prescription drugs currently used as therapeutic agents for obesity are sibutramine ('REDUCTIL from Abbott) and Orlistat (Xenical form Roche). Sibutramine blocks the reabsorption of noradrenaline and serotonin, thereby regulating appetite and reducing dietary intake. However, sibutramine is a substance having a property of acting on the central nervous system, and thus has side effects that affect heartbeat, blood pressure, and the like. In contrast to sibutramine, orlistat acts locally. As an inhibitor of lipase of the stomach and the small intestine, orlistat acts to inhibit the hydrolysis of fat. Therefore, about 30% of the fat taken from the food and drink is not absorbed into the body and is discharged, thus achieving a weight adjustment effect. However, undigested fat moves along the gastrointestinal track and causes side effects such as diarrhea and steatorrhea, which make the body not only uncomfortable, but also difficult to perform in normal social life.

Therefore, there is an urgent need in the art to develop a new, non-toxic side-effect medicament for the treatment and prevention of obesity and related diseases.

SUMMARY OF THE INVENTION

Another object of the present invention is to provide the use of *Christensenella intestinihominis* for the treatment and prevention of obesity and related diseases.

Another object of the present invention is to provide a pharmaceutical, beverage, food composition, or animal feed composition for the treatment and prevention of obesity and related diseases thereof, which is effective and has no toxic side effects.

Another object of the present invention is to provide a method of reducing body weight and/or blood lipids and uses thereof.

In the first aspect of the present invention, it provides a *Christensenella intestinihominis*, the *Christensenella intestinihominis* is a *Christensenella intestinihominis*.

In another preferred embodiment, the *Christensenella intestinihominis* is an intestinal *Christensenella intestinihominis*.

In another preferred embodiment, the sequence of the 16s rDNA of the *Christensenella intestinihominis* is as shown in SEQ ID NO.: 1.

In another preferred embodiment, the *Christensenella intestinihominis* is *Christensenella intestinihominis* AF73-05CM02 with a deposit number of CGMCC 1.5207.

In the second aspect of the present invention, it provides a composition, which comprises: (a) a safe and effective amount of *Christensenella intestinihominis* according to the first aspect of the present invention and/or metabolites thereof; and (b) a food acceptable carrier or a pharmaceutically acceptable carrier.

In another preferred embodiment, the composition is selected from the group consisting of: a food composition, a health care composition, a pharmaceutical composition, a beverage composition, a feed composition, and a combination thereof.

In another preferred embodiment, the composition is an oral preparation.

In another preferred embodiment, the composition is a liquid preparation, a solid preparation, or a semi-solid preparation.

In another preferred embodiment, the dosage form of the composition is selected from the group consisting of a powder, pulvis, tablet, sugar coating agent, capsule, granule, suspension, solution, syrup, drop, and sublingual tablet.

In another preferred embodiment, the food composition comprises an emulsion product, a solution product, a powder product, or a suspension product.

In another preferred embodiment, the food composition comprises a dairy product, milk powder, or lotion.

In another preferred embodiment, the liquid preparation is selected from the group consisting of a solution product or a suspension product.

In another preferred embodiment, the composition comprises $1\times10\text{-}1\times10^{10}$ cfu/mL or cfu/g of *Christensenella intestinihominis* AF73-05CM02, preferably $1\times10^4\text{-}1\times10^{10}$ cfu/mL or cfu/g of *Christensenella intestinihominis* AF73-05CM02, based on the total volume or total weight of the composition.

In another preferred embodiment, the composition comprises from 0.0001 to 99 wt %, preferably from 0.1 to 90 wt % of the *Christensenella intestinihominis* and/or the metabolites thereof, based on the total weight of the composition.

In another preferred embodiment, the composition is in a unit dosage form (one tablet, one capsule or one vial) and the mass of the composition in each unit dosage form is from 0.05 to 5 g, preferably from 0.1 to 1 g.

In another preferred embodiment, the composition further comprises other probiotics and/or prebiotics.

In another preferred embodiment, the probiotic is selected from the group consisting of lactic acid bacteria, bifidobacteria, *Lactobacillus acidophilus*, and a combination thereof.

In another preferred embodiment, the prebiotic is selected from the group consisting of fructooligosaccharide (FOS), galactooligosaccharide (GOS), xylooligosaccharide (XOS), lactosucrose (LACT), soybean oligosaccharides (SOS), Inulin, and a combination thereof.

In the third aspect of the present invention, it provides a use of the *Christensenella intestinihominis* according to the first aspect of the present invention, or the composition according to the second aspect of the present invention for the preparation of a medicament or preparation, which is used for one or more of the uses selected from the group consisting of: (a) prevention and/or treatment of obesity; (b) reduction of blood lipids; (c) prevention or treatment of cardiovascular disease; and/or (d) prevention and/or treatment of diabetes.

In another preferred embodiment, the preparation comprises a microecological preparation.

In the fourth aspect of the present invention, it provides a use of the *Christensenella intestinihominis* according to the first aspect of the present invention, or the composition according to the second aspect of the present invention for the preparation of a medicament or preparation, which is used for one or more of the uses selected from the group consisting of:
  (i) reducing cholesterol levels in mammals;
  (ii) inhibiting the weight gain of mammals;
  (iii) reducing the body fat ratio of the mammals;
  (iv) reducing blood lipid levels in mammals;
  (v) increasing the level of high density lipoprotein (HDL-C) in mammals;
  (vi) reducing the level of low density lipoprotein (LDL-C) in mammals.

In another preferred embodiment, the mammals comprise humans or non-human mammals.

In another preferred embodiment, the non-human mammals comprise rodents (such as rats, or mice).

In another preferred embodiment, the reduction of blood lipid levels in mammals comprises the reduction of total cholesterol (TC) level and/or triglyceride level.

In the fifth aspect of the present invention, it provides a method for preparing the composition according to the second aspect of the present invention, comprising a step of:
  mixing the *Christensenella intestinihominis* according to the first aspect of the present invention and/or the metabolites thereof with a food acceptable carrier or a pharmaceutically acceptable carrier, thereby forming a composition according to the second aspect of the present invention.

In another preferred embodiment, the composition is an oral preparation.

In the sixth aspect of the present invention, it provides a production method, comprising the following steps:

(a) cultivating the *Christensenella intestinihominis* according to the first aspect of the present invention under a condition suitable for culturing, thereby obtaining a culture product;
  (b) optionally, isolating *Christensenella intestinihominis* bacteria cells and/or metabolites thereof from the culture product; and
  (c) optionally, mixing the obtained *Christensenella intestinihominis* bacteria cells and/or the metabolites isolated from the previous step with a food acceptable carrier or pharmaceutically acceptable carrier, thereby obtaining a composition.

In the seventh aspect of the present invention, it provides a method for reducing weight and/or blood lipid levels, comprising administering the *Christensenella intestinihominis* according to the first aspect of the present invention and/or metabolites thereof or the composition according to the second aspect of the present invention to a subject.

In another preferred embodiment, the administration comprises oral administration.

In another preferred embodiment, dosage for administering is 0.01-5 g/50 kg body weight/day, preferably is 0.1-2 g/50 kg body weight/day.

In another preferred embodiment, the subject comprises a mammal, such as a human.

It should be understood that, within the scope of the present invention, each technical feature of the present invention described above and in the following (as examples) may be combined with each other to form a new or preferred technical solution, which is not listed here due to space limitations.

DETAILED DESCRIPTION

Through extensive and intensive research and experiments, the inventors have unexpectedly discovered that *Christensenella intestinihominis* has the function of preventing and treating obesity and related diseases (such as cardiovascular diseases, diabetes). The active composition containing *Christensenella intestinihominis* was fed to the test subject, and the composition was found to inhibit weight gain, reduce blood fat levels, reduce cholesterol levels, reduce body fat ratio, reduce low density lipoprotein levels, increase high density lipoprotein levels, and effectively alleviate conditions of obesity, cardiovascular, diabetes and other diseases. On this basis, the inventors completed the present invention.

As used herein, the term "comprising" means that various ingredients may be together employed in a mixture or composition of the present invention. Thus, the term "consisting essentially of" and "consisting of" are encompassed in the term "comprising".

*Christensenella intestinihominis* and Use Thereof

As used herein, the terms "the strain *Christensenella intestinihominis*", "*Christensenella intestinihominis*" can be used interchangeably. In a preferred embodiment, the strain is *Christensenella intestinihominis* AF73-05CM02 with a deposit number of CGMCC 1.5207, isolated from human feces. Physiological characteristics of *Christensenella intestinihominis* are shown as follows. The *Christensenella intestinihominis* cultured in an anaerobic environment at 37° C. for 4-5 days has needle-like, gray-white, transparent small colonies with about 0.2 mm in diameter, and it was observed under microscope at magnification 1000 after Gram staining and spore staining, the bacteria cells are Gram-positive, short rod-shaped, without spores, without flagella, without movement, and with a diameter of about 0.5 um, a length of about 1.0-2.0 um, and the bacterium presents a single cell or short chain, and the oxidase and catalase reactions of the *Christensenella intestinihominis* of the present invention are both negative. The temperature growth range is 30-42° C. and the optimum growth temperature is 37-42° C. The pH tolerance range is 6.0-8.5 and the optimum pH is 6.5-7.0, and it can withstand 2% of NaCl and 3% of bile salts. It can ferment several carbohydrates, including glucose, mannitol, maltose, salicyl alcohol, xylose, arabinose, mannose, pine syrup, raffinose, sorbitol, rhamnose. In addition, extracellular polysaccharides can be produced by fermentation, formic acid, acetic acid and butyric acid are mainly produced.

The present invention provides the use of the *Christensenella intestinihominis* in the treatment and prevention of obesity and related diseases such as cardiovascular disease, diabetes. For the subject ingesting a high-fat diet, the strain *Christensenella intestinihominis* AF73-05CM02 has one or more uses selected from the group consisting of: (i) inhibiting weight gain in the subject; (ii) reducing blood lipid levels; (iii) reducing body lipid ratio; (iv) reducing low density lipoprotein levels; (v) increasing high density lipoprotein levels. According to a preferred embodiment of the present invention, C57BL/6J male mice were used as test mice, and fed with a high-fat diet to become obese mice. Compared with the untreated control group (model group), obese mice treated with the strain *Christensenella intestinihominis* AF73-05CM02 had a slower weight gain and decreased blood lipid levels and various indicators related to obesity or cardiovascular disease were also decreased, such as body fat ratio, low density lipoprotein levels, and in addition, high-density lipoprotein levels had also been increased significantly. Therefore, the strain can be used for the prevention and treatment of obesity and related diseases (such as cardiovascular disease, diabetes, etc.).

Composition and the Use Thereof

The present invention also provides a composition, preferably a pharmaceutical composition. The composition comprises an effective amount of *Christensenella intestinihominis*. In a preferred embodiment, the composition further comprises the probiotics selected from the group consisting of: lactic acid bacteria, bifidobacteria, *Lactobacillus acidophilus*, and a combination thereof; and/or prebiotics selected from the group consisting of: fructooligosaccharide (FOS), galactooligosaccharide (GOS), xylooligosaccharide (XOS), lactosucrose (LACT), soybean oligosaccharides (SOS), Inulin, and a combination thereof.

In a preferred embodiment, the composition is a liquid preparation, a solid preparation, or a semi-solid preparation.

In a preferred embodiment, the liquid preparation is selected from the group consisting of a solution product or a suspension product.

In a preferred embodiment, the dosage form of the composition is selected from the group consisting of a powder, pulvis, tablet, sugar coating agent, capsule, granule, suspending agent, solution, syrup, drop, and sublingual tablet.

The pharmaceutical composition of the present invention may be administered in any form selected from the group consisting of a pharmaceutical tablet, injection and capsule. The pharmaceutical preparation comprises an excipient, and a pharmaceutically acceptable vehicle or a carrier, and these substances may be selected according to the administration route. The pharmaceutical preparations in the present invention may further contain auxiliary active ingredients.

Lactose, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, or mineral oil and the like can all be used as a carrier, an excipient or a diluent and the like in the pharmaceutical composition of the present invention.

In addition, the pharmaceutical composition of the present invention may further include a lubricant, wetting agent, emulsifying agent, suspension stabilizer, preservative, sweetener and fragrance and the like. The pharmaceutical composition of the present invention can be produced as enteric-coated preparations by various well-known methods so that the active ingredient of the pharmaceutical composition, that is, the microorganisms, can smoothly pass through the stomach without being destroyed by gastric acid.

In addition, the microorganism of the present invention can be used in the form of a capsule prepared by a conventional method. For example, a standard excipient is mixed with the freezing-dried microorganisms of the present invention to form a pellet pill, and then the pill is filled into a gelatin capsule. Further, the microorganisms of the present invention can be mixed with a pharmaceutically acceptable excipient, such as a liquid gum, cellulose, silicate or mineral oil and the like to prepare a suspension or a dispersion liquid, which can be filled into a soft gelatin capsule.

The pharmaceutical composition of the present invention can be made into enteric-coated tablets for oral use. The term "enteric coating" in the present invention includes all the conventional and pharmaceutically acceptable coatings. These coatings cannot be degraded by gastric acid but can be sufficiently decomposed in the small intestine and release the microorganisms of the present invention rapidly. The enteric coating of the present invention can be maintained in a synthetic gastric acid solution, such as HCl solution (pH=1), for more than 2 hours at 36-38° C. and preferably can be decomposed within 1.0 hour in a synthetic intestinal fluid, such as a buffer with a pH of 7.0.

The enteric coating of the present invention is about 16-30 mg, preferably 16-25 mg, more preferably 16-20 mg, per tablet. The thickness of the enteric coating in the present invention is 5-100 µm, and the ideal thickness is 20-80 µm. The ingredient of the enteric coating is selected from conventional polymers that are well known in the art.

The preferred enteric coating of the present invention can be prepared from a copolymer of a cellulose acetate phthalate polymer or a trimellitate polymer and a methacrylic acid (for example, a methacrylic acid copolymer containing 40% or more of methacrylic acid and methylcellulose hydroxypropyl phthalate or the ester derivatives thereof).

The cellulose acetate phthalate used in the enteric coating of the present invention has a viscosity of about 45-90 cp. The content of the acetyl is 17-26%, and the content of orthophthalic acid is 30-40%. The cellulose acetate diphenyl ester used in the enteric coating has a viscosity of about 5-21 cs. The content of acetaphthalein is 17-26%. The cellulose acetate trimellitate manufactured by Eastman Keda Company can be used for the enteric coating materials in the present invention.

The hydroxypropylmethylcellulose phthalate used in the enteric coating of the present invention typically has a molecular weight of 20,000-130,000 Daltons, and the ideal molecular weight is 80,000-100,000 Daltons. The content of the hydroxypropyl is 5-10%. The methoxy content is 18-24%, and the phthaloyl content is 21-35%.

The hydroxypropylmethylcellulose phthalate used in the enteric coating of the present invention is HP50, produced by Shin-Etsu Chemical Co., Ltd., Japan. HP50 contains 6-10% of hydroxypropyl, 20-24% of methoxy, and 21-27% of propyl, with a molecular weight of 84,000 Daltons. Another enteric coating material is HP55, which contains 5-9% of hydroxypropyl methylcellulose phthalate, 18-22% of methoxy, and 27-35% of phthalic acid, with a molecular weight of 78,000 Daltons.

The enteric coating of the invention is prepared by spraying the enteric coating solution onto the core using conventional methods. All of the solvents used in the enteric coating process are selected from alcohols (such as ethanol), ketones (such as acetone), halogenated hydrocarbon compounds (such as methylene chloride), and the combinations thereof. The softener, such as di-n-butyl phthalate and triacetin, is added into the enteric-coated solution at a ratio of about 1 part of the coating to about 0.05 parts or about 0.3 parts of softener. The spraying is preferably continuously carried out and the amounts of spraying materials can be controlled according to the conditions used for the coating. Spraying pressure can be adjusted randomly. In general, the desired results can be obtained at an average pressure of 1-1.5 bar.

The term "pharmaceutically effective amount" in the specification refers to an amount that is functional and active to human and/or animals and acceptable to human and/or animals. For example, in the present invention, a preparation containing $1\times10$-$1\times10^{10}$ cfu/ml or cfu/g (particularly, $1\times10^4$-$1\times10^{10}$ cfu/ml or cfu/g; more particularly, $1\times10^6$-$1\times10^{10}$ cfu/ml or cfu/g) of *Christensenella intestinihominis* and/or a metabolite thereof can be prepared.

When used for the preparation of pharmaceutical compositions, the effective dosage of *Christensenella intestinihominis* or the metabolites thereof may vary depending on the mode of administration and the severity of the disease to be treated. Dosage forms suitable for oral administration include about $1\times10$-$1\times10^{10}$ cfu/ml or cfu/g (particularly, $1\times10^4$ to $1\times10^{10}$ cfu/ml or cfu/g; more particularly $1\times10^6$ to $1\times10^{10}$ cfu/ml or cfu/g) of the active *Christensenella intestinihominis* or fermentation-produced active ingredients, in a close mixture with a solid or a liquid pharmaceutically acceptable carrier. This dosing regimen can be adjusted to provide the best therapeutic response. For example, depending on the urgency of the treatment condition, several divided doses may be administered daily, or the dose may be proportionally reduced.

The *Christensenella intestinihominis* or the metabolites thereof can be administered by oral administration and the like. Solid carriers include starch, lactose, dicalcium phosphate, microcrystalline cellulose, sucrose and kaolin, while liquid carriers include: mediums, polyethylene glycol, non-ionic surfactants and edible oils (such as corn oil, peanut oil, and sesame oil), as long as it is suitable for the properties of the *Christensenella intestinihominis* or the metabolites thereof and the desired particular mode of administration. Adjuvant commonly used in the preparation of pharmaceutical compositions may also be advantageously included, such as flavors, coloring agents, preservatives and antioxidants such as vitamin E, vitamin C, BHT and BHA.

In order to facilitate preparation and administration, the preferable pharmaceutical composition is a solid composition, especially a tablet and a solid-filled or liquid-filled capsule. Oral administration is preferred.

The composition of the present invention is administered to the individual one or more times per day. The dosage unit means that the dose is formally separable and suitable for human or other mammalian individual. Each unit contains a pharmaceutical acceptable carrier and a therapeutically effective amount of the microorganism of the present invention. The amount to be administered varies with the weight of the patient, the severity of the obesity, the cardiovascular diseases or the diabetes, the included supplementary active components and the employed microorganisms. In addition, if possible, it can be administered separately and, if necessary, it can be administered continuously. Thus, the amounts for administration will not limit the invention. In addition, the "composition" in the present invention not only means medicine but also means functional food and health supplements. In a preferred embodiment, the composition comprises: beverages, foods, medicines, animal feeds and the like.

In a preferred embodiment of the present invention, a food composition is further provided, comprising an effective amount of *Christensenella intestinihominis* and/or a metabolite thereof, and the rest food acceptable carrier. The dosage form of the food composition is selected from the group consisting of a solid, dairy product, solution product, powder product, and suspension product.

In a preferred embodiment, the formulation of the composition is shown as follows:

$1\times10$-$1\times10^{10}$ cfu/mL of *Christensenella intestinihominis* and/or the metabolites thereof; and a food or pharmaceutically acceptable carrier, and/or an excipient.

In another preferred embodiment, the formulation of the composition is shown as follows:

$1\times10^6$-$1\times10^{10}$ cfu/mL of *Christensenella intestinihominis* and/or the metabolites thereof; and a food or pharmaceutically acceptable carrier, and/or an excipient.

Microecological Preparation

The microecological preparation is a biological preparation containing probiotics and metabolites thereof or a dietary supplement which can increase probiotics. And it can achieve the purpose of improving human health by regulating and maintaining the microecological balance in the intestinal tract. It mainly includes probiotics, prebiotics and synbiotics.

In the present invention, the microecological preparation comprises (a) a safe and effective amount of the *Christensenella intestinihominis* and/or the metabolite thereof; and (b) a food acceptable carrier or a pharmaceutically acceptable carrier.

Production Method for *Christensenella intestinihominis*

Generally, *Christensenella intestinihominis* can be prepared by conventional methods.

In the present invention, a method capable of producing *Christensenella intestinihominis* on a large scale is provided. In particular, the following steps are included:

(a) under conditions suitable for culturing, cultivating *Christensenella intestinihominis*, thereby obtaining a culture product;

(b) optionally, isolating the *Christensenella intestinihominis* bacteria cells and/or metabolites thereof from the culture product; and (c) optionally, mixing the isolated *Christensenella intestinihominis* bacteria cells and/or their metabolites obtained in the previous step with a food acceptable carrier or pharmaceutically acceptable carrier, thereby obtaining the composition.

Method for Reducing the Weight and/or Blood Lipid

In another preferred embodiment, the method comprises: administering a pharmaceutical composition, a food composition, a beverage composition of the present invention, or a combination thereof. The subject is human.

In another preferred embodiment, the method comprises: administering a pharmaceutical composition, a food composition, or an animal feed of the invention, or a combination thereof. The subjects are animals, preferably mice and rabbits.

Deposit of Microorganisms

The strain of *Christensenella intestinihominis* (*Christensenella intestinihominis* AF73-05CM02) (with the same deposit name) of the present invention has been deposited at the China General Microbiological Culture Collection Center (CGMCC, address: No. 3, NO. 1 of West Beichen Road, Chaoyang District, Beijing, China) on Jun. 13, 2016. The deposit number is CGMCC1.5207.

The main advantages of the present invention include:

(a) The *Christensenella intestinihominis* of the present invention can significantly reduce body weight, reduce blood fat levels, and reduce body fat ratio.

(b) The *Christensenella intestinihominis* of the present invention can significantly reduce indicators (such as levels of cholesterol and triglycerides) associated with obesity and its related diseases such as cardiovascular diseases.

(c) The *Christensenella intestinihominis* of the present invention is capable of significantly lowering the levels of total cholesterol, triglycerides, and low density lipoprotein.

(d) The *Christensenella intestinihominis* of the present invention can significantly increase the level of high density lipoprotein.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise stated, the materials used in the examples are all commercially available products.

*Christensenella minuta* DSM 22607 (*C. minuta* DSM 22607), hereinafter referred to as DSM 22607, was purchased from the German Collection of Microorganisms and Cultures under the deposit number of DSM 22607.

Example 1 Screening and Identification of Intestinal *Christensenella intestinihominis* AF73-05CM02 (Hereinafter Referred to as AF73-05CM02)

1. Isolation of AF73-05CM02

The intestinal *Christensenella intestinihominis* AF73-05CM02 of the present invention was isolated from a stool sample of a healthy male volunteer in Shenzhen. Approximately 0.2 g of stool sample was taken in an anaerobic operation box, suspended in sterile PBS, shaken and mixed, and then subjected to gradient dilution coating. The separation medium was PYG medium (purchased from Huan Kai Microbiology Technology Co., Ltd.) 1 L: peptone 5 g, pancreatic casein 5 g, yeast powder 10 g, beef extract 5 g, glucose 5 g, $K_2HPO_4$ 2 g, Tween 80 1 mL, Cysteine-$HCl.H_2O$ 0.5 g, heme 5 mg, vitamin $K_1$ 1 uL, inorganic salt solution ($CaCl_2.2\ H_2O$ 0.25 g, $MgSO_4.7\ H_2O$ 0.5 g, $K_2HPO_4$ 1 g, $KH_2PO_4$ 1 g, $NaHCO_3$ 10 g, NaCl 2 g was contained in each L of inorganic salt solution) 40 mL, resazurin 1 mg, distilled water 950 mL, pH 6.8~7.0, sterilized at 115° C. for 25 min. After the plate was cultured at 37° C. for 5 days under anaerobic conditions, single colonies were picked for separation, and the gas composition of the anaerobic environment was nitrogen:hydrogen:carbon dioxide=90:5:5, v/v. Pure culture strains were obtained through streak cultivation and subjected to glycerol preservation and 16S rDNA identification.

2. Microbiological Characteristics of AF73-05CM02

(1) Morphological Characteristics

Figure 2:
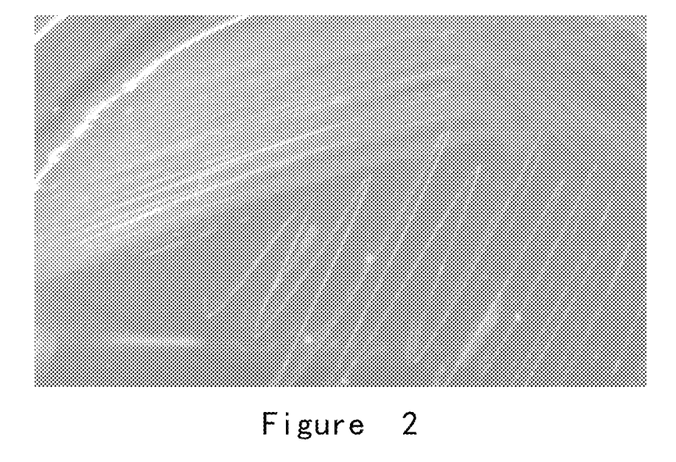
FIG. 2 shows a picture of colonies of intestinal *Christensenella intestinihominis* cultured for 4 days.

After culturing for 4-5 days at 37° C. in anaerobic conditions, the colonies of AF73-05CM02 on PYG plates were small, about 0.2 mm in diameter, needle-like, grayish-white, and transparent (FIG. 2).

(2) Microscopic Features

Figure 1:
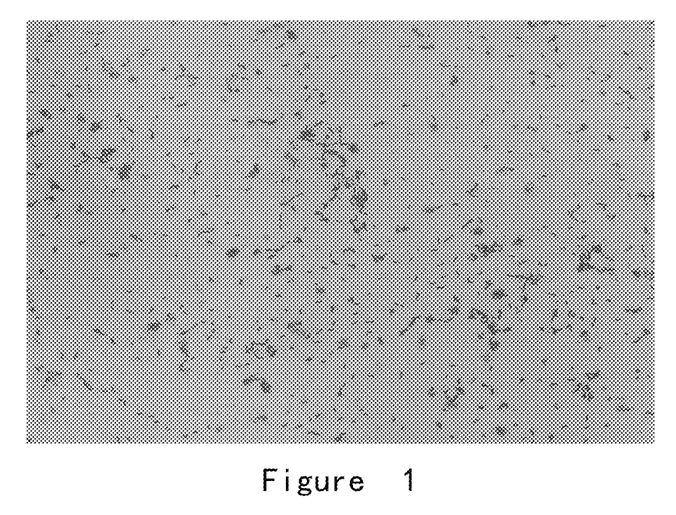
FIG. 1 is a Gram stained picture (1000 times) of the intestinal *Christensenella intestinihominis* of the present invention under the microscope.

Through Gram staining and spore staining, it was observed under a microscope at 1000 magnification. The bacteria cells were Gram-positive, short rod-shaped, without spores, without flagella, without movement. The diameter of the bacteria cells was about 0.5 um, and the length was about 1.0-2.0 um, and the bacterium presents a single bacteria cell or short chain (FIG. 1).

(3) Physiological and Biochemical Characteristics

AF73-05CM02 was negative for catalase and negative for oxidase. The temperature growth range was 30-42° C., and optimum growth temperature was 37-42° C. The pH tolerance range was 6.0-8.5, and optimum pH was 6.5-7.0, and it was able to tolerate 2% NaCl and 3% bile salts. The comparison of biochemical reaction of enzyme reaction (API ZYM) and substrate utilization (API 20A) between AF73-05CM02 and a nearby model strain of *Christensenella minuta* DSM 22607 (hereinafter referred to as DSM 22607, purchased from the German Collection of Microorganisms and cell cultures, DSMZ) was as follows: (+, indicating a positive reaction; −, indicating a negative reaction; w, indicating a weak positive reaction).

TABLE 1

| substrate | AF73-05CM02 | *Christensenella minuta* DSM 22607 |
|---|---|---|
| API 20A | | |
| Tryptophan (production of indole) | − | − |
| urea (urease) | − | − |
| glucose | + | + |
| mannitol | w | w |
| lactose | − | − |
| sucrose | − | − |
| maltose | w | − |
| salicyl alcohol | w | + |
| xylose | + | + |
| arabinose | + | + |
| Gelatin hydrolysis | − | − |
| esculin/ferric citrate | + | − |
| glycerinum | − | − |
| cellobiose | − | − |
| mannose | + | w |
| pine syrup | w | − |
| raffinose | w | − |

TABLE 1-continued

| substrate | AF73-05CM02 | Christensenella minuta DSM 22607 |
|---|---|---|
| sorbitol | + | + |
| rhamnose | + | + |
| trehalose | − | − |
| API ZYM | | |
| Control | − | − |
| alkaline phosphatase | − | − |
| esterase (C4) | − | − |
| lipid esterase (C8) | − | − |
| lipid enzyme (C14) | − | − |
| Leucine arylamine | − | − |
| Valine arylase | − | − |
| cystinarylase | − | − |
| trypsin | − | − |
| chymotrypsin | − | − |
| acid phosphatase | − | − |
| naphthol-AS-BI-phosphohydrolase | + | + |
| α-galactosidase | − | − |
| β-galactosidase | − | − |
| β-uronic acid chymase | − | − |
| α-glucosidase | − | − |
| β-glucosidase | − | + |
| N-acetyl-glucosamine | − | − |
| α-mannosidase | − | − |
| β-fucosidase | − | − |

The data in Table 1 showed that there was a partial difference in the API reaction between AF73-05CM02 and the closely related model bacteria, which is reflected in the utilization of maltose, salicyl alcohol, mannose, pine syrup and raffinose, hydrolysis of esculin and β-glucosidase activity.

3. Identification of 16S rDNA

AF73-05CM02 was cultured to a stationary phase, and 2 mL of the cultured bacterial solution was taken for genomic DNA extraction. The 16S rDNA was amplified using the extracted genomic DNA as a template, and the amplification primers were 8F-1492R (5'-AGAGTTTGATCATG-GCTCAG-3' (SEQ ID NO.: 2) and 5'-TAGGGTTACCTTGTTACGACTT-3' (SEQ ID NO.:3)).

The amplification procedure was:

```
94° C.    4 min
94° C.    30 s      ⎫
65° C.-57° C. 40 s  ⎬ 20 cycles
72° C.    1 min and 30 s ⎭
94° C.    30 s      ⎫
57° C.    40 s      ⎬ 10 cycles
72° C.    1 min and 30 s ⎭
72° C.    10 min
4° C.     ∞
```

The amplified PCR product was purified, and then subjected to 3730 sequencing to obtain a 1366 bp of 16S rDNA sequence (SEQ ID NO.: 1). The sequence was subjected to EzTaxon-e database alignment to preliminary obtain the species classification information of the strain. According to the information of 16S rDNA, it can be preliminarily determined that AF73-05CM02 belongs to the genus Christensenella.

```
SEQ ID No.: 1
ttgctctttg tgaagccctc gggtggaact gcgagtatac ttagtggcgg acgggtgagt    60
aacgcgtgag caatctgccc tgcaatgggg gacaacagtt ggaaacgact gctaataccg   120
catgagacca cgaaaccgca tggttttgag gtaaaaggat ttattcgatg caggatgagc   180
tcgcgtccca ttagatagtt ggtgaggtaa cggcccacca agtcaacgat gggtagccga   240
cctgagaggg tgatcggcca cactggaact gagacacggt ccagactcct acgggaggca   300
gcagtgggga atattgggca atgggggaaa ccctgaccca gcaacgccgc gtgagggaag   360
aaggtcttcg gattgtaaac ctttgtccta tgggacgaaa caaatgacgg taccatagga   420
ggaagctccg gctaactacg tgccagcagc cgcggtaata cgtagggagc aagcgttgtc   480
cggaattact gggcgtaaag ggtgcgtagg tggctatgta agtcagatgt gaaagaccgg   540
ggcttaaccc cggggttgca tttgaaactg tgtggcttga gtacaggaga gggaagtgga   600
attcctagtg tagcggtgaa atgcgtagat attaggagga acaccagtgg cgaaggcgac   660
tttctggact gtaactgaca ctgaagcacg aaagcgtggg gagcaaacag gattagatac   720
cctggtagtc cacgccgtaa acgatggata ctaggtgtgg gcccgatag ggttccgtgc   780 cgaagctaac gcattaagta tcccgcctgg ggagtacgat cgcaaggttg aaactcaaag   840
gaattgacgg gggcccgcac aagcagcgga gcatgtggtt taattcgaag caacgcgaag   900
aaccttacca aggcttgaca tcctctgacg actgtagaga tacagtttcc cttcggggca   960
gagagacagg tggtgcatgg ttgtcgtcag ctcgtgtcgt gagatgttgg gttaagtccc  1020
gcaacgagcg caacccttat tgctagttgc cagcgcgtaa aggcgggaac tctagtgaga  1080
ctgccgggga caactcggag gaaggtgggg acgacgtcaa atcatcatgc cccttatgtc  1140
ttgggctaca cacgtgctac aatggccggt acaaagggca gcgaaccccg aaggggaagc  1200
```

```
gaatctcaaa aagccggtcc cagttcggat tgtgggctgc aacccgccca catgaagtcg  1260
gagttgctag taatcgcgaa tcagcatgtc gcggtgaatg cgttcccggg ccttgtacac  1320
accgcccgtc acaccacgga agttgggagc acccgaagcc agtgga               1366
```

4. Evolutionary Analysis of AF73-05CM02

Multiple sequence alignment was performed for sequences of AF73-05CM02 and model strains in EzTaxon-e databases whose 16S rDNA sequences were close to that of AF73-05CM02. Then the evolutionary tree was made with MEGA 5, and the phylogenetic tree was constructed using the maximum likelihood method.

5. Analysis of Cellular Fatty Acid Contents

AF73-05CM02 and C. minuta DSM 22607 were cultured, and the bacteria cells were collected after about 4-5 days, and the cellular fatty acids were extracted, then subjected to methyl esterification, and the fatty acid methyl ester contents of the two strains were analyzed by gas chromatography.

TABLE 2

| Fatty acids | Chinese name | AF73-05CM02 | DSM 22607 |
|---|---|---|---|
| $C_{10:0}$ | deca-saturated fatty acid | 7.50 | 8.57 |
| $C_{11:0}$ iso | hetero-11 carbon saturated fatty acid | 5.55 | 2.89 |
| $C_{11:0}$ anteiso | anti-isolated eleven carbon saturated fatty acid | 0 | 1.31 |
| $C_{12:0}$ | dodecane saturated fatty acid | 7.15 | 1.13 |
| $C_{13:0}$ anteiso | anti-isolated tri-carbon saturated fatty acid | 0 | 2.35 |
| $C_{14:0}$ | fourteen carbon saturated fatty acid | 46.57 | 13.03 |
| $C_{15:0}$ iso | heterogenous fifteen carbon saturated fatty acid | 7.40 | 27.40 |
| $C_{15:0}$ anteiso | anti-isoform fifteen carbon saturated fatty acid | 1.29 | 3.19 |
| $C_{14:0}$ 2OH | 2-hydroxytetradecane saturated fatty acid | 0 | 1.25 |
| $C_{16:0}$ | hexadecane saturated fatty acid | 9.66 | 21.14 |
| $C_{17:1}$ iso I/anteiso B | type I-isotype/B type-anti-isotype seventeen carbon unsaturated fatty acid | 4.65 | 1.68 |
| $C_{18:0}$ antei/$C_{18:2}$ ω6,9c | anti-isomorphic eighteen carbon saturated fatty acid/ω6,9c-eighteen carbon diunsaturated fatty acid | 0 | 1.68 |
| $C_{18:1}$ ω9c | ω9c-18 carbon monounsaturated fatty acid | 6.92 | 6.76 |
| $C_{18:1}$ ω7c | ω7c-Octadecene monounsaturated fatty acid | 0 | 3.92 |
| $C_{18:0}$ | Octadecyl saturated fatty acid | 1.80 | 3.73 |

Based on the above data, the above morphological, microscopic, physiological and biochemical characteristics and 16S rDNA sequence characteristics of AF73-05CM02, it is indicated that the strain is a new species from a taxonomic perspective, and it was named as *Christensenella intestinihominis* (intestinal *Christensenella intestinihominis*) in the present invention.

Example 2 Bioactive Substances of the Intestinal *Christensenella intestinihominis* AF73-05CM02

1. Production and Determination of Active Substances Such as Short Chain Fatty Acids (SCFA) and Organic Acids (1) Sample Pretreatment 1 mL of the fermentation solution of AF73-05CM02 cultured for 72 hours was taken and centrifuged at 12000 r/min for 5 min, and the supernatant was aspirated for use.

(2) Determination of SCFA

The short-chain fatty acid was determined by an external standard method, in which acetic acid, propionic acid, butyric acid, and pentanoic acid were used to prepare a standard curve. Agilent Meteorological Chromatograph (GC-7890B, Agilent) and HP-INNOWax (Cross-Linked PEG), 30 m×0.25 mm×0.25 um capillary column were used for analysis. The detector was a hydrogen flame ion detector, and the GC parameter was set to column temperature: 180~200° C.; gasification chamber temperature: 240° C.; detection temperature: 210° C.; injection volume: 2 μL; carrier gas flow rate: $N_2$, 50 mL/min; hydrogen flow rate: 50 mL/min; air flow rate: 600~700 ml/min.

The yield of SCFA was determined to be 5.21 mmol/L for formic acid, 16.40 mmol/L for acetic acid and 1.63 mmol/L for butyric acid.

(3) Determination of Organic Acids 3-methylbutyric acid, pentanoic acid, quininic acid, lactic acid, oxalic acid, malonic acid, benzoic acid, maleic acid, succinic acid, fumaric acid, malic acid, adipic acid, tartaric acid, shikimic acid, citric acid, isocitric acid and L-ascorbic acid were selected as the standard samples for determination of organic acids. Agilent Meteorological Chromatograph (GC-7890B, Agilent) was still used. The chromatographic column was 122-5532G DB-5 ms (40 m×0.25 mm×0.25 um), wherein the column temperature was 270~290° C.; inlet temperature was 250° C.; gas flow rate was 0.86 ml/min. The contents of the organic acid of intestinal *Christensenella intestinihominis* AF73-05CM02 were shown in the following table:

TABLE 3

| | organic acid | | | | | |
|---|---|---|---|---|---|---|
| | 3-methylbutyric acid | pentanoic acid | quininic acid | lactic acid | oxalic acid | malonic acid |
| content (mmol/L) | 0.37 | 0.36 | 0 | 4.13 | 0 | 0 |
| | organic acid | | | | | |
| | benzoic acid | maleic acid | succinic acid | fumaric acid | malic acid | adipic acid |
| content (mmol/L) | 0 | 0 | 0.37 | 0 | 0 | 0.24 |

TABLE 3-continued

| | organic acid | | | | |
|---|---|---|---|---|---|
| | tartaric acid | shikimic acid | citric acid | isocitric acid | L-ascorbic acid |
| content (mmol/L) | 0 | 0 | 0.18 | 0 | 0.11 |

Example 3: In Vitro Degradation Function of Cholesterol by *Christensenella intestinihominis* AF73-05CM02

Figure 3:
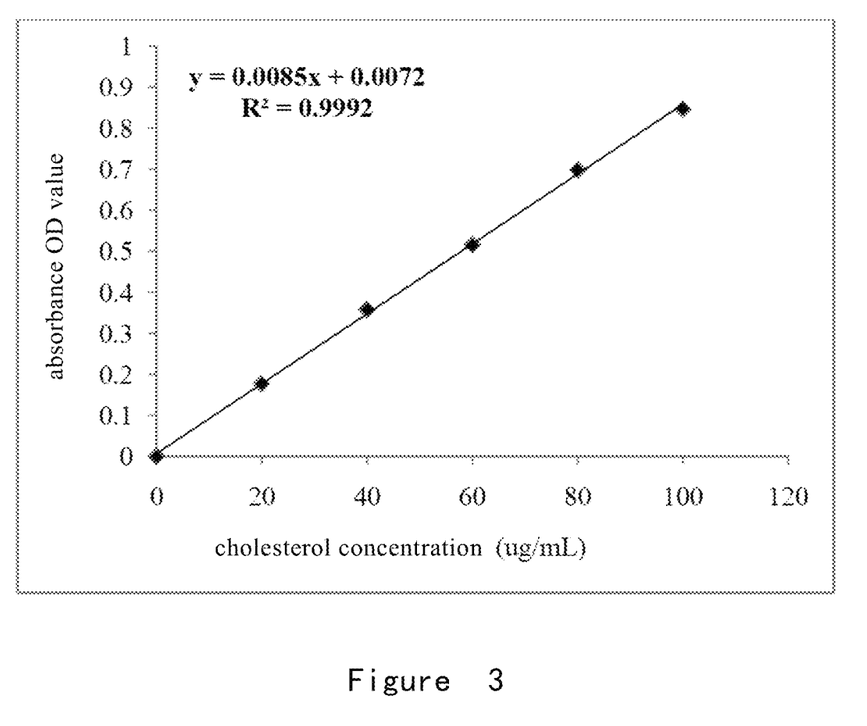
FIG. 3 shows a standard curve for cholesterol determination.

The method for determining the content of cholesterol is performed using the o-phthalaldehyde colorimetric method (OPA method). The degradation ability of cholesterol was examined by the change of the cholesterol content of the strain in a medium containing a certain concentration of cholesterol for a period of time. The specific method was as follows:

(1) Production of Standard Curve 0.5 mg/mL cholesterol standard solution for 40 uL, 80 uL, 120 uL, 160 uL, 200 uL was accurately measured and placed in a clean tube. Absolute ethanol was added to make the volume 1 mL. 4 mL of OPA (0.5 mg phthalaldehyde was added to 1 mL glacial acetic acid) was added to each tube, and it was shaken and mixed, placed for 10 min at room temperature. Then 2 mL of concentrated sulfuric acid was added and reacted for 10 min, and the absorbance was measured at 550 nm. Using the concentration as the abscissa and the absorbance as the ordinate to draw a standard curve (FIG. 3). By calculation, the equation for linear regression is: y=0.0085x+0.0072; the correlation coefficient $R^2$ is 0.9992.

(2) Preparation of Cholesterol Medium and Cultivation of Experimental Strains

A certain amount of cholesterol was weighed and dissolved in ethanol at a concentration of 10 mg/mL, and sterilized by filtration. 10 mg/mL bile salt (autoclaving), 10% mass concentration of sodium thioglycollate (filtration sterilization) and cholesterol were added into the prepared PYG medium (formulation was the same as in Example 1) and mixed well, and then the test strain was inoculated into the medium according to the inoculation amount of 3%, and cultured under anaerobic conditions at 37° C. for 72 h.

(3) Determination of Cholesterol

The bacterial solution cultured in PYG medium containing the cholesterol was centrifuged at 10000 r/min, and the supernatant was collected for cholesterol detection, and the uninoculated cholesterol PYG medium was used as a blank control. 500 ul of the sample to be tested was placed in a clean test tube, and 3 ml of 95% ethanol and 2 ml of 50% KOH were added, shaken and mixed, then subjected to saponification reaction in a 60° C. water bath for 10 min, rapidly cooled. 5 ml of n-hexane was added for extraction. 2.5 ml of organic phase was placed to another clean test tube, then dried in nitrogen in a 60° C. water bath. 4 ml of 0.5 g/L phthalaldehyde acetic acid solution was added for color development for 10 min. 2 ml concentrated $H_2SO_4$ was added for 10 min, and finally the absorbance at 550 nm was measured.

(4) Calculation of Cholesterol Degradation Rate

The degradation of cholesterol was calculated according to the following formula:

$$L=(A-B)/A\times100\%$$

L: cholesterol degradation rate;
A: cholesterol content in cholesterol medium without inoculation;
B: cholesterol content after culture of the bacteria.

(5) Cholesterol Degradation Results

By calculation, the cholesterol degradation rate of AF73-05CM02 was 46.6%. The results showed that AF73-05CM02 had a certain ability to degrade cholesterol and can be further used in animals for research.

Example 4 Detection of Extracellular Polysaccharides Produced by Intestinal *Christensenella intestinihominis* AF73-05CM02

The detection of extracellular polysaccharides was carried out by the sulfuric acid-phenol method. The sulfuric acid-phenol can react with hexoses in the free monosaccharides, oligosaccharides and polysaccharides for the chromogenic reaction, and the color produced was proportional to the absorbance, whose absorption wavelength was 490 nm. The specific experimental process was as follows:

(1) Extraction of Polysaccharides

The experimental strain was cultured in PYG medium (formulation was the same as in Example 1) for 3 days. 10 ml of bacterial solution was treated in boiling water bath for 30 min, then centrifuged at 10000 r/min, and the supernatant was removed and 80% trichloroacetic acid was added to a final concentration of 8%. The protein was precipitated by treatment at 4° C. overnight. It was centrifuged at 10,000 r/min for 30 min, and the pH of supernatant was adjusted to 6.0 with NaOH. Double volume of absolute ethanol was added to precipitate the polysaccharide. It was treated at 4° C. overnight and taken out and centrifuged at 10000 r/min for 30 min. The supernatant was discarded. The precipitate was dissolved with preheated distilled water, and transferred to the ultrafiltration tube (3000 Da filter diameter) for the ultrafiltration. It was subjected to centrifugation at 5000 r/min for 30 min. The polysaccharide intercepted in the inner tube was transferred to a volumetric flask added with distilled water to a volume of 10 ml, and for use.

(2) Production of Glucose Standard Curve 20 mg of the standard glucose was accurately weighed and placed to 100 ml volumetric flask, and water was added to the scale line, and then 20, 40, 60, 80, 100 μg/ml glucose standard solution was formulated respectively. 400 ul was taken from each group of standard solution, three in parallel, and then 400 ul of 5% phenol and 1 ml of concentrated sulfuric acid were sequentially added to carry out the reaction, and the mixture was cooled to room temperature in a boiling water bath for 15 minutes, and the absorbance at 490 nm was measured. Then, the absorbance was taken as the ordinate, and the glucose standard solution concentration was taken as the abscissa for the standard curve.

(3) Detection of the Concentration of the Extracted Polysaccharide 400 ul of the polysaccharide solution was taken, and 400 ul of 5% phenol and 1 ml of concentrated sulfuric acid were successively added to carry out the reaction. The mixture was cooled to room temperature after a boiling water bath for 15 minutes, and the absorbance at 490 nm was measured. The concentration of the polysaccharide was calculated according to the glucose standard curve.

(4) Results

By calculation, the content of extracellular polysaccharide in the fermentation solution of AF73-05CM02 cultured for 3 days was 234 mg/L.

Example 5 In Vivo Test of Intestinal *Christensenella intestinihominis* AF73-05CM02 in an Animal Model of Obesity Preparation of Experimental Animals and Test Strains:

Experimental animals: C57BL/6J male mice were used and purchased from Guangdong Medical Laboratory Animal Center. Normal feeding, at the age of 6 weeks. A total of 30 mice were randomly divided into 3 groups for 10 animals each. The rat room environment was of SPF (Specific Pathogen Free) level.

Test strain: normal cultured AF73-05CM02. The medium was PYG liquid medium (formulation was the same as in Example 1). It was cultured under anaerobic conditions for 3 days at 37° C., and the concentration of bacteria was about $10^9$ CFU/mL, which can be used as an experimental group for gavage. In order to prevent the bacteria from inactivating or even dying, the fresh bacterial liquid was replaced every other day, and The bacterial liquid was stored under anaerobic conditions at 4° C.

The experimental procedure: The newly purchased mice were randomly divided into 3 groups. The first group was the control group, the second group was the obesity model group (model group), and the third group was the bacterial treatment group. Mice in the first group were fed a normal diet, while mice in the second and third groups were fed a high-fat diet (for obesity model modeling). After 5 weeks of feeding, mice in the third group began to undergo an intragastric intervention using AF73-05CM02. Mice in the first group and the second group were intragastrically administrated with the same amount of medium for 9 weeks. The amount of the gavage bacteria solution was 0.15 mL/10 g body weight. The body weight, status, and food intake of the mice were recorded weekly before and after the intervention and the modeling. At the end of the experiment, the mice were sacrificed. The fat content was recorded, and the serum was collected, and the serum lipid content, including total cholesterol (TC), triglyceride (TG), high-density lipoprotein (HDLC), and low density lipoprotein (LDLC) was measured according to the kit instructions.

Experimental Results:

1. Effect of AF73-05CM02 on Weight Gain of Obese Model Mice

TABLE 4-1

| Group numbering | weight gain after 1 week (g) | weight gain after 5 weeks (g) | weight gain after 9 weeks (g) |
| --- | --- | --- | --- |
| Group one | 1.73 ± 0.58 | 4.87 ± 0.55 | 6.05 ± 0.85 |
| Group two | 2.40 ± 0.42 | 7.98 ± 0.72 | 12.45 ± 0.79 |
| Group three | 1.89 ± 0.36 | 4.87 ± 0.55 | 8.58 ± 0.98 |

TABLE 4-2

| Group numbering | weight gain after 9 weeks (g) | P value-Model group | P value-Control group |
| --- | --- | --- | --- |
| Group one (Control group) | 6.05 | 0.000* | 1.000 |
| Group two (Model group) | 12.45 | 1.000 | 0.000* |
| Group three (Bacterial treatment group) | 8.58 | 0.001* | 0.075 |

By comparing the changes in body weight gain of mice after 9 weeks in the experimental group (Table 4-1 and Table 4-2), it can be found that AF73-05CM02 gavage intervention can effectively slow down the increase of weight gain in mice (*P<0.05).

2. Effect of AF73-05CM02 on Body Fat Ratio of Obese Model Mice

TABLE 5

| Group numbering | Fat weight/body weight × 100% (body fat ratio) | P value-Model group | P value-Control group |
| --- | --- | --- | --- |
| Group one | 2.625 | 0.000* | 1.000 |
| Group two | 7.848 | 1.000 | 0.000* |
| Group three | 3.768 | 0.000* | 0.054 |

The results in Table 5 showed that AF73-05CM02 could significantly reduce the body fat ratio of obese model mice (*P<0.05).

3. Effect of AF73-05CM02 on Blood Lipid Levels in Experimental Mice

TABLE 6-1

| Group numbering | TC (total cholesterol) (mmol/L) | TG (triglyceride) (mmol/L) | LDLC (low density lipoprotein) (mmol/L) | HDLC (high-density lipoprotein) (mmol/L) |
| --- | --- | --- | --- | --- |
| Group one | 3.527 | 0.852 | 1.431 | 3.251 |
| Group two | 6.823 | 1.342 | 2.561 | 2.386 |
| Group three | 4.621 | 1.005 | 1.479 | 3.326 |

TABLE 6-2

| P value | TC (total cholesterol) | TG (triglyceride) | LDLC (low density lipoprotein) | HDLC (high-density lipoprotein) |
| --- | --- | --- | --- | --- |
| AF73-05CM02-Model group (group three-group two) | 0.000* | 0.001* | 0.006* | 0.039* |
| AF73-05CM02-Control group (group three-group one) | 0.094 | 0.316 | 0.521 | 0.699 |
| Model-Control group (group two-group one) | 0.005* | 0.031* | 0.015* | 0.042* |

The results in Table 6-1 and Table 6-2 showed that the intervention of AF73-05CM02 (Group 3) can effectively control the levels of TC, TG, LDLC in the blood and increase HDLC level (*P<0.05). The main components of blood lipids are cholesterol and triglycerides. The increase of cholesterol and triglyceride levels in plasma is closely related to the occurrence of atherosclerosis. The main function of high-density lipoprotein was to remove excess cholesterol and low-density lipoprotein from blood and cells and has anti-atherosclerosis effect. Therefore, AF73-05CM02 can lower blood lipid levels, reduce the related indicators of atherosclerosis-related diseases (such as cardiovascular disease), and also significantly increase the level of high-density lipoprotein.

Example 6 Food Composition Containing Intestinal *Christensenella intestinihominis* AF73-05CM02

The raw materials were shown in Table 7.

TABLE 7

| Raw material | mass percent (%) |
|---|---|
| *Christensenella intestinihominis* AF73-05CM02 | 0.5 |
| milk | 90.0 |
| sugar | 9.5 |

Milk and sugar were mixed according to the above formula ratio, stirred until completely mixed, preheated, homogenized at 20 Mpa, sterilized for 5-10 minutes at 90° C., cooled to 40-43° C. 1-100×10$^6$ cfu/g of *Christensenella intestinihominis* AF73-05CM02 bacteria was inoculated. Thus a food composition containing *Christensenella intestinihominis* AF73-05CM02 was obtained.

Example 7 Pharmaceutical Composition Containing *Christensenella intestinihominis*

The ratio of raw materials was shown in Table 8.

TABLE 8

| Raw material | mass percent(%) |
|---|---|
| *Christensenella intestinihominis* AF73-05CM02 | 1.0% |
| lactose | 2.0% |

TABLE 8-continued

| Raw material | mass percent(%) |
|---|---|
| yeast powder | 2.0% |
| peptone | 1.0% |
| purified water | 94.0% |

According to the ratio, lactose, yeast powder and peptone were mixed uniformly with purified water, preheated to 60-65° C., homogenized at 20 Mpa, sterilized at 90° C. for 20-30 minutes, and cooled to 36-38° C. and *Christensenella intestinihominis* AF73-05CM02 live bacteria (1-50×10$^6$ cfu/mL) was inoculated, fermented to pH 6.0 at 36-38° C., centrifuged, and lyophilized to a moisture content of less than 3% to prepare a lyophilized product of *Christensenella intestinihominis* AF73-05CM02. 0.5 g of *Christensenella intestinihominis* AF73-05CM02 lyophilizate was weighed and mixed in equal amounts with maltodextrin and filled into capsules to prepare a pharmaceutical composition containing *Christensenella intestinihominis* AF73-05CM02.

Deposit of Microorganisms

The strain of *Christensenella intestinihominis* (*Christensenella intestinihominis* AF73-05CM02) (with the same deposit name) of the present invention has been deposited at the China General Microbiological Culture Collection Center (CGMCC, address: No. 3, NO. 1 of West Beichen Road, Chaoyang District, Beijing, China) on Jun. 13, 2016. The deposit number is CGMCC1.5207.

All publications mentioned herein are incorporated by reference as if each individual document was cited as a reference in the present application. It should also be understood that, after reading the above teachings of the present invention, those skilled in the art can make various changes or modifications, equivalents of which falls in the scope of claims as defined in the appended claims.

The invention claimed is:

1. A method of treating obesity or obesity related diseases, which comprises a step of: administering a *Christensenella intestinihominis* or a composition comprising the *Christensenella intestinihominis* to a subject in need, wherein the *Christensenella intestinihominis* has a sequence of 16s rDNA as set forth in SEQ ID NO: 1.

2. The method of claim 1 wherein the *Christensenella intestinihominis* or the composition comprising *Christensenella intestinihominis* exhibits any activities from of the group consisting of:
   (i) reducing cholesterol levels in mammals;
   (ii) reducing the weight gain of mammals;
   (iii) reducing the body fat ratio of the mammal;
   (iv) reducing blood lipid levels in mammals;
   (v) increasing the level of high density lipoprotein (HDL-C) in mammals; and
   (vi) reducing the level of low density lipoprotein (LDL-C) in mammals.

3. The method of claim 2, wherein the reduction of blood lipid levels in mammals comprises the reduction of total cholesterol (TC) level and/or triglyceride level.

4. The method of claim 1, wherein the *Christensenella intestinihominis* is *Christensenella intestinihominis* AF73-05CM02 with a deposit number of CGMCC 1.5207.

5. The method of claim 1, wherein the obesity related diseases are cardiovascular diseases or diabetes.

6. The method of claim 1, wherein the subject includes human or non-human mammal.

7. The method of claim 1, wherein the composition further comprises a food acceptable or pharmaceutically acceptable carrier.

8. The method of claim 1, wherein the composition further comprises probiotics and/or prebiotics.

9. The method of claim 8, wherein the probiotics are selected from the group consisting of *Lactobacillus*, *Bifidobacteria*, *Lactobacillus acidophilus*, and a combination thereof, and
   the prebiotics are selected from the group consisting of fructooligosaccharide (FOS), galactooligosaccharide (GOS), xylooligosaccharide (XOS), lactosucrose (LACT), soybean oligosaccharides (SOS), Inulin and a combination thereof.

10. The method of claim 1, wherein the composition comprises $1\times10$-$1\times10^{10}$ cfu/mL or cfu/g of *Christensenella intestinihominis* AF73-05CM02, based on the total volume or total weight of the composition.

11. The method of claim 1, wherein the composition comprises $1\times10^4$-$1\times10^{10}$ cfu/mL or cfu/g of *Christensenella intestinihominis* AF73-05CM02, based on the total volume or total weight of the composition.

12. The method of claim 1, wherein the composition is selected from the group consisting of a food composition, a health care composition, a pharmaceutical composition, a beverage composition, a feed composition and a combination thereof.

13. The method of claim 1, wherein the composition is administered orally.

14. The method of claim 1, wherein the administration dosage of the composition is 0.01-5 g/50 kg body weight/day.

15. The method of claim 1, wherein the composition is in a unit dosage form of one tablet, one capsule or one vial, and the mass of the composition in each unit dosage form is of the weight from 0.05 to 5 g.

16. The method of claim 7, wherein the food acceptable or pharmaceutically acceptable carrier is selected from excipient, lubricant, wetting agent, emulsifier, suspension stabilizer, preservative, sweetener and fragrance.

17. The method of claim 1, wherein the composition is of a dosage form selected from the group consisting of powder, pulvis, tablet, sugar coating agent, capsule, granule, suspension, solution, syrup, drop and sublingual tablet.

18. A production method, comprising the following steps:
(a) cultivating an isolated *Christensenella intestinihominis* under anaerobic conditions with a liquid medium at a temperature of 30 to 42° C. and pH of 6.0 to 8.5, thereby obtaining a culture product, wherein the *Christensenella intestinihominis* has a sequence of 16s rDNA as set forth in SEQ ID NO: 1,
(b) isolating *Christensenella intestinihominis* bacteria cells from the culture product, and
(c) mixing the *Christensenella intestinihominis* bacteria cells isolated in the step (b) with a food acceptable or pharmaceutically acceptable carrier, thereby obtaining a composition.

19. The production method of claim 18, wherein the *Christensenella intestinihominis* is *Christensenella intestinihominis* AF73-05CM02 with a deposit number of CGMCC 1.5207.

* * * * *

UNITED STATES PATENT AND TRADEMARK OFFICE
CERTIFICATE OF CORRECTION

PATENT NO. : 10,806,759 B2
APPLICATION NO. : 16/082873
DATED : October 20, 2020
INVENTOR(S) : Yuanqiang Zou et al.

Page 1 of 1

It is certified that error appears in the above-identified patent and that said Letters Patent is hereby corrected as shown below:

In the Claims

Column 21, Lines 55-56, replace "activities from of the" with --activities from the--

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 3

<210> SEQ ID NO 1
<211> LENGTH: 1366
<212> TYPE: DNA
<213> ORGANISM: Christensenella intestinihominis AF73-05CM02

<400> SEQUENCE: 1

```
ttgctctttg tgaagccctc gggtggaact gcgagtatac ttagtggcgg acgggtgagt      60
aacgcgtgag caatctgccc tgcaatgggg gacaacagtt ggaaacgact gctaataccg     120
catgagacca cgaaaccgca tggttttgag gtaaaaggat ttattcgatg caggatgagc     180
tcgcgtccca ttagatagtt ggtgaggtaa cggcccacca agtcaacgat gggtagccga     240
cctgagaggg tgatcggcca cactggaact gagacacggt ccagactcct acgggaggca     300
gcagtgggga atattgggca atgggggaaa ccctgaccca gcaacgccgc gtgagggaag     360
aaggtcttcg gattgtaaac ctttgtccta tgggacgaaa caaatgacgg taccatagga     420
ggaagctccg gctaactacg tgccagcagc cgcggtaata cgtagggagc aagcgttgtc     480
cggaattact gggcgtaaag ggtgcgtagg tggctatgta agtcagatgt gaaagaccgg     540
```

```
ggcttaaccc cggggttgca tttgaaactg tgtggcttga gtacaggaga gggaagtgga    600
attcctagtg tagcggtgaa atgcgtagat attaggagga acaccagtgg cgaaggcgac    660
tttctggact gtaactgaca ctgaagcacg aaagcgtggg gagcaaacag gattagatac    720
cctggtagtc cacgccgtaa acgatggata ctaggtgtgg ggcccgatag ggttccgtgc    780
cgaagctaac gcattaagta tcccgcctgg ggagtacgat cgcaaggttg aaactcaaag    840
gaattgacgg gggcccgcac aagcagcgga gcatgtggtt taattcgaag caacgcgaag    900
aaccttacca aggcttgaca tcctctgacg actgtagaga tacagtttcc cttcggggca    960
gagagacagg tggtgcatgg ttgtcgtcag ctcgtgtcgt gagatgttgg gttaagtccc   1020
gcaacgagcg caacccttat tgctagttgc cagcgcgtaa aggcgggaac tctagtgaga   1080
ctgccgggga caactcggag gaaggtgggg acgacgtcaa atcatcatgc cccttatgtc   1140
ttgggctaca cacgtgctac aatggccggt acaaagggca gcgaacccgt aaggggaagc   1200
gaatctcaaa aagccggtcc cagttcggat tgtgggctgc aacccgccca catgaagtcg   1260
gagttgctag taatcgcgaa tcagcatgtc gcggtgaatg cgttcccggg ccttgtacac   1320
accgcccgtc acaccacgga agttgggagc acccgaagcc agtgga              1366

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
agagtttgat catggctcag                                                 20

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
tagggttacc ttgttacgac tt                                              22
```